United States Patent [19]

Cruz, Jr.

[11] 4,405,324

[45] Sep. 20, 1983

[54] ABSORBENT CELLULOSIC STRUCTURES

[75] Inventor: Mamerto M. Cruz, Jr., Pennington, N.J.

[73] Assignee: Morca, Inc., Pennington, N.J.

[21] Appl. No.: 295,768

[22] Filed: Aug. 24, 1981

[51] Int. Cl.³ .............................................. A61F 13/00
[52] U.S. Cl. .................................... 604/376; 604/356; 604/368
[58] Field of Search ............... 128/284, 287, 290 R, 128/296, 156; 604/376, 377, 374–375, 368, 356

[56] References Cited

U.S. PATENT DOCUMENTS

| | | | |
|---|---|---|---|
| 3,005,456 | 10/1961 | Graham, Jr. | 128/285 |
| 3,067,745 | 12/1962 | Burgeni et al. | 128/285 |
| 3,094,494 | 6/1963 | Hopkins et al. | 128/285 |
| 3,371,666 | 3/1968 | Lewing | 128/285 |
| 3,431,909 | 3/1969 | Krusko | 128/285 |
| 3,520,302 | 7/1970 | Jones | 128/285 |
| 3,723,413 | 3/1973 | Chatterjee et al. | 128/285 |
| 3,935,099 | 1/1976 | Weaver et al. | 128/285 |
| 4,292,972 | 10/1981 | Pawelchak et al. | 128/296 |

OTHER PUBLICATIONS

The Merck Index, 9th Ed., 1976, p. 259.

*Primary Examiner*—C. Fred Rosenbaum
*Attorney, Agent, or Firm*—George F. Mueller

[57] ABSTRACT

Absorbent, coherent, flexible structures in the form of fibrous webs and porous sponges comprising cellulose derivatives having a DS of between about 0.05 and about 0.35 whereby upon application to the body and wet with aqueous body liquids, the protruding fibers and fibrils or hairs become highly swollen or may dissolve thereby eliminating irritation. The derivative may be such as to impart hemostatic properties and the structure may include uniformly dispersed therein chitin and/or starch derivatives to enhance the hemostatic efficacy. The structures may include water-soluble agents which function as dry binders but when the structure is wet with aqueous body liquids, the agents dissolve and become leached from the structures.

14 Claims, No Drawings

ABSORBENT CELLULOSIC STRUCTURES

This invention relates to absorbent, coherent bodies or structures based upon cellulose as a precursor raw material.

Cellulose based bodies or structures, such as, for example, regenerated cellulose sponge, cellulose gauze (cotton or regenerated cellulose fiber), structureless masses of loose cellulose (cotton and regenerated cellulose) fibers and the like have been utilized to absorb body liquids and blood for medical purposes, as in a variety of surgical procedures. Although, in general, these bodies or structures are relatively inexpensive, the principal disadvantage in their use in contact with tender or sensitive areas of the body, as in the eye, abrasions, incisions and the like, is the stiffness, harshness and scratchy nature of cellulose sponges and fibers which may result in irritation. The harshness and stiffness, in some instances, may cause a rupture in the skin or membrane allowing harmful microorganisms to enter the wound. Conventional regenerated cellulose sponge contains reinforcing fibers. When the sponge is cut to desired sizes, the cut surfaces present sharp edges where the film-like structure has been severed and, in addition, fine fiber fragments are formed along the cut surfaces. In the use of such cut sponges, as in the conventional pledgets used in eye treatment and surgery, the fine fibers protruding from the cut surfaces and the cut surfaces cause irritation and loose fiber fragments may become dislodged and serve as additional sources of irritation and where the skin or membrane is broken serve as a source of infection. Further the dislodged fiber fragments may enter the incision or wound thereby introducing into the body foreign material.

The present invention provides absorbent, coherent and flexible cellulosic structures which overcome the disadvantages of the prior products without detracting from the liquid absorbency of the prior products.

The present invention further provides absorbent, coherent and flexible cellulosic structures having a higher liquid absorbency than the prior products.

The present invention also provides absorbent, coherent cellulosic structures, such as cut sponges, for example, pledgets, wherein the protruding fibers, macrofibrils or "hairs" and the sharp edges of the sponge, when the structure is applied to the body and wet with aqueous body liquids, become almost instantaneously extremely high swollen or, in some instances, dissolved thereby avoiding any possible harshness or irritation.

The present invention also further provides absorbent, coherent cellulosic structures containing water soluble impregnants which may serve as binding agents in the dry state of the structure, but when wet with body liquids dissolve and become leached from the structure, as in pledgets used in eye treatment or surgical procedures and the solution serves as a lubricant.

The present invention also contemplates structures which are not only absorbent but also posses hemostatic properties.

Further advantages will become apparent from the detailed description and examples which follow.

The present invention contemplates coherent, water-insoluble but water-swellable derivatized cellulose structures with or without water-soluble impregnants having dry binding properties. The cellulosic bases are cellulose ethers, cellulose mixed ethers and cellulose ether mixed esters having a total degree of substitution (DS) of from about 0.05 to about 0.35, preferably between about 0.1 and about 0.25. The specific DS varies within the broad range depending upon the specific derivative. For example, in the case of carboxymethyl cellulose, the DS may vary within the broad range but preferably lies within the range of 0.1 to 0.25. In the case of derivatives such as cellulose succinate, glutarate, maleate and the like, the DS preferably is within the range of from about 0.05 to about 0.3. In the case of mixed ethers, such as, for example, hydroxypropylmethyl cellulose, the total DS preferably varies from about 0.05 to about 0.25 wherein the methyl substitution may be 0.05–0.15 and the hydroxypropyl substitution may be 0.05–0.1. In the case of a cellulose ether mixed ester such as, for example, succinylated methyl cellulose, the methyl substitution may be from 0.05 to 0.2, preferably 0.1–0.15, and the succinyl substitution may be from 0.1 to 0.2. The succinate ester is utilized so as to impart to the coherent cellulosic structures hemostatic properties. The ether substituents are primarily utilized to impart swelling characteristics.

The coherent structures are in sponge and fibrous mat forms. The sponge forms may be prepared in accordance with the conventional method of producing cellulosic sponges by the viscose process or the conventional methods of producing such sponges from cellulose esters. Following thorough washing and purification of these types of sponges, the sponge comprising the porous cellulose structure and contained cellulose reinforcing fibers is derivatized. Alternatively, a sponge-like structure may be formed by freeze drying an aqueous-organic solvent slurry of cellulose derivative fibers. The fibrous mat structures may be formed by any desired conventional method normally used to prepare non-woven cellulose fiber mats followed by derivatizing the cellulose fibers which may be natural or regenerated cellulose. Alternatively, the cellulose fibers may first be derivatized prior to forming the non-woven mat. Preferably, the derivatized fibers are dispersed or slurried in a liquid medium comprising water and a water-miscible organic solvent such as, for example, ethanol, isopropanol, acetone and the like. The mat is formed by sheeting the fibers and freeze drying the mat, preferably pressing the sheeted fiber mat to expel excess liquid prior to freeze drying.

Derivatization of the cellulosic base may be effective in any conventional manner. Agents useful in derivatization are known and include compounds, such as, for example, ethylene oxide, propylene oxide, butylene oxide, methyl chloride, ethyl chloride, chloroacetic acid, methyl chloride and ethylene oxide, methyl chloride and propylene oxide (the combination for the preparation of ether-esters), succinic anhydride, glutaraldehyde, maleic anhydride and the like.

For the preparation of fibrous mats, any desired cellulosic fibers such as chemically purified wood pulp fibers, cotton linters, regenerated cellulose fibers and the like are satisfactory. Preferably, the raw material is highly fibrillated, chemically purified wood pulp having a CSF (Canadian Standard Freeness) not exceeding about 150, but preferably 50 or below. This type of raw material is highly fibrillated and derivatization results in a product of higher absorbency. Also the coherent fibrous mat will possess a greater proportion of protruding macrofibrils and microfibrils or "hairs" which ar more readily derivatized and hence more rapidly highly swollen when wet with body liquids. Although the fibers may be first formed into the coherent mat and then derivatized, preferably the fiber raw material is derivatized prior to converting the fibers into a coherent mat. By first derivatizing the fibers a more uniformly derivatized structure is obtained. In view of the fact that in most instances derivatized fibers are more sensitive to aqueous liquids, in forming the sheeted webs or mats, the derivatized fibers are slurried in a liquid medium comprising water and a water-miscible organic solvent. The relative proportions of water and organic solvent are varied depending upon the specific DS of the derivatized cellulosic fiber. In general, the higher the DS, the greater the proportion of the organic solvent, as will be apparent from the examples. The use of the water-organic solvent media is essential so as to provide the coherent structure with the desired compactness, flexibility and absorbency. Because of the water sensitivity of the derivatized fibers, slurrying of such fibers in water alone while resulting in highly coherent mats, the mats are harsh and stiff and of low absorbency.

The following examples illustrate the preparation of derivatized cellulosic fibers of low DS, of coherent mats formed therefrom and the characteristics of the fibers and coherent mats.

EXAMPLE 1-3

In the preparation of carboxymethyl cellulose fibers, highly fibrillated, chemically purified wood pulp fibers (CSF of about 50) were utilized. 30 Grams of the pulp fibers were slurried in 722 gms. of an aqueous liquid consisting of azeotropic isopropanol. In each instance various volumes of a 20% caustic soda solution were added to the slurries while the slurries were at ambient temperature. In order to obtain the stated DS of the carboxymethyl cellulose fibers, stated amounts of chloroacetic acid dissolved in 8 gms. of 100% isopropanol were added to the slurries. The mixtures were then heated to 50° to 55° C. and maintained at the elevated temperature for 5 hours while mildly agitating the slurries. The derivatized fibers were recovered by filtration and the recovered fibers washed by slurrying in azeotropic isopropanol and again recovered by filtration. The washing procedure was repeated three times. Each washing was effected by slurrying the fibers in about 300 mls. of the azeotrope. The finally recovered fibers were then slurried in about 250 mls. of 100% isopropanol. The fibers recovered from the final washing were vacuum dried at 45°-50° C. The fibers as thus prepared comprise a sodium salt of carboxymethyl cellulose. If desired, following the derivatization step, appropriate amounts of an acid such as hydrochloric acid may be added to convert the sodium salt to the free acid form.

In the preparation of air dried, coherent mats, samples of the dried fibers were slurried in both water-ethanol and water-isopropanol media to form slurries of approximately 0.1% consistency. The fibers were sheeted on a 100 mesh sieve and the major portion of the liquid media removed by suction. Another 100 mesh sieve was placed over the formed sheet and a pulp sheet blotter placed over the upper sieve and a like pulp sheet blotter placed beneath the lower sieve. A 3 pound roll was passed over the assembly to expel excess liquid. The sheet was removed and dried in a circulating air oven at 45° C.

In the preparation of freeze dried coherent mats or sheets, the same procedure was followed except the samples of the dried derivatized fibers were slurried in media containing lower proportions of the organic solvents to form slurries of about 10% consistency. Following the pressing to expel excess liquid the mats or sheets were freeze dried.

As a control, 30 grams of the wood pulp fibers were subjected to washings with azeotropic isopropanol and 100% isopropanol and vacuum dried at 45°-50° C. Samples of the dried fibers were slurried in water-ethanol and water-isopropanol media and mats formed as described for the preparation of mats from the derivatized fibers.

The physical properties of the mats as prepared are reported in Table I. The sample mat sizes, thickness values and weights as set forth in the table are averages of at least 6 samples of mats prepared as described. It will be noted that the mats prepared from slurries of the derivatized fibers in ethanol-water media and isopropanol-water media are substantially identical in the physical properties and, hence, only single values are set forth in the table.

Table II sets forth the properties exhibited by microscopic observations at a magnification of 400× when samples of the webs and of the fibers were wetted with an isotonic saline solution. Again, the observations for webs prepared from ethanol-water and isopropanal-water media and when air dried and freeze dried are substantially identical.

As shown by the data in Tables I and II, when preparing slurries for the formation of mats, in order to avoid producing a high degree of bonding between the fibers, the higher the DS of the fibers, the greater the relative proportion of the alkanol required in the slurrying liquid. Also, in order to provide sheets or mats having substantially identical physical properties dried by air drying requires a higher proportion of the alkanol than those dried by freeze drying. The data further illustrates that when mats and fibers are wetted with an aqueous liquid, the higher the DS of the fibers, the greater the degree of swelling. Although the cellulose fibers of the control mats when wetted exhibit "hairs" protruding from the fiber surfaces and ends, no such "hairs" are visible on the wetted cellulose derivative fibers. The lumen width of the wetted cellulose fibers is not altered, the reduction in the lumen width varies directly with the DS of the derivatized fibers. Similarly, the fiber width increases directly with the DS. When the wetted fiber is placed between glass plates and pressure is applied, the flattening of the fibers increases directly with the DS.

EXAMPLE 4

In the preparation of hydroxypropylmethyl cellulose fibers, the same highly fibrillated, chemically purified wood pulps fibers are used in Examples 1-3 were utilized. Methyl cellulose fibers were first prepared by slurrying 25 parts of the pulp fibers in 20 parts of a 20% solution of caustic soda and about 700 parts of azeotropic isopropanol by mixing for about 30 minutes in a closed vessel. A mixture of 4 parts of methyl chloride in about 8 parts of azeotropic isopropanol was introduced into the vessel and mixing continued for about 2.5 hours while maintaining the mixture at a temperature of 30°-35° C. Approximately 4 parts of propylene oxide in 4 parts of azeotropic isopropanol was then introduced into the vessel and the mass agitated for an additional 4.5 hours while maintaining the mass at a temperature of 35°-40° C.

The hydroxypropylmethyl cellulose fibers were recovered by filtration and washed by slurrying in azeotropic isopropanol and separated by filtration. Washing was repeated three times. Following this washing procedure, the fibers were subjected to a final wash with 100% isopropanol. Where the product is intended for use in surgical procedures, the isopropanol in the reaction mixture is replaced with ethanol, the first four washing steps utilizing 200 proof (100%) ethanol. The ethanol substitution is utilized because it is difficult to remove traces of isopropanol. Following washing, the fibers may be dried in an air circulating oven at about 50° C., but preferably vacuum dried at 45°–50° C. The derivatized fibers thus prepared had a methyl substitution equivalent to a DS of 0.1–0.15 and a hydroxypropyl substitution equivalent to a DS of 0.05–0.1. The total substitution is equivalent to a DS of about 0.15 to about 0.26. In order to insure removal of all sodium hydroxide in appropriate amount of an acid such as hydrochloric acid may be added to the fibers recovered from the reaction mass prior to washing. It is obvious that by varying the amounts of methyl chloride and propylene oxide, the relative degrees of methyl and hydroxypropyl substitution may be varied as desired. In all instances, however, the total substitution should not exceed a total DS of about 0.3.

Coherent mats and sheets may be formed in the same manner as described in Examples 1–3. Alternatively, following final washing, the derivatized fibers need not be dried but may be slurried directly in aqueous isopropanol or aqueous ethanol to form dilute slurries as described in Examples 1–3. Coherent mats formed from slurries in the two media are substantially identical to properties. The microscopic observations at a magnification of 400× when the mats are wet with a 0.9% saline solution are substantially identical to those observed for Example 2.

EXAMPLE 5

In the preparation of succinylated carboxymethyl cellulose, carboxymethyl cellulose of a DS of 0.1–0.13 was prepared as described in Example 1. A mixture of 4 parts of succinic anhydride, 10 parts of sodium acetate and 80 parts of glacial acetic acid was prepared. To this mixture, 30 parts of the carboxymethyl cellulose fibers were added and the mass agitated for about 3 hours at 35°–40° C. The succinylated carboxymethyl cellulose fibers were recovered by filtration and the fibers washed with ethanol or isopropanol as described in Example 4. The fibers had a succinyl substitution equivalent to a DS of 0.1–0.2. Similar succinylated carboxymethyl cellulose fibers were also prepared by the use of carboxymethyl cellulose fibers as described in Examples 2 and 3. Obviously, succinylated carboxymethyl cellulose fibers having succinyl substitution of higher DS may be prepared by increasing the relative amounts of succinic anhydride. In all instances, however, the total substitution should not exceed about a DS of about 0.35.

Coherent mats may be prepared as described in Examples 1–4. Mats formed from slurries in aqueous ethanol and aqueous isopropanol are substantially identical in properties. Microscopic observations of the succinylated carboxymethyl cellulose fibers as prepared above are substantially identical to those of Example 2.

Conventional regenerated cellulose sponge is formed from a mixture of viscose, reinforcing fibers, for example, regenerated cellulose fibers, cotton, linen and the like and a pore forming salt high in water of crystallization. This class of salt includes sodium sulfate decahydrate, sodium carbonate decahydrate, trisodium phosphate decahydrate, sodium acetate trihydrate, potassium sodium tartrate tetrahydrate and the like. The viscose may contain from 5 to 8% cellulose, 6 to 100% fibers, based on the cellulose, and 900 to 2500% of the pore forming salt, based on the cellulose. The pore size in the sponge is directly related to the size of the pore forming salt crystals. As is conventional, the viscose mixture is cast in a desired mold, the cellulose solution coagulated, usually by heat, and the cellulose then regenerated. The shaped mass is then washed thoroughly to remove soluble salts, desulphurized and bleached.

EXAMPLE 6

Sponge was prepared from viscose containing 6% cellulose, 7% caustic soda, 30% carbon bisulfide, based on cellulose, 25% of the highly fibrillated chemically purified wood pulp fibers and 1500% sodium sulfate decahydrate. The preparation of derivatized sponge structures followed the procedure utilized in forming the derivatized fibers. In the preparation of carboxymethyl cellulose sponge (regenerated cellulose and cellulose reinforcing fibers), four 1.8 gm. samples of sponge, each about 6 cm.×6 cm.×0.7 cm., were submerged in 400 ml. of azeotropic isopropanol. In each instance various volumes of a 20% caustic soda solution were added and the sponges agitated in the liquid for about $\frac{3}{4}$ hour. Various amounts of chloroacetic acid in 8 gms. of isopropanol were added and the sponges agitated in the liquid for 2$\frac{1}{2}$ to 3 hours while maintaining the temperature at 50°–55° C.

The derivatized sponges were removed from the liquid, the liquid allowed to drain and the excess liquid then expressed from the sponges. The sponges were then treated with dilute isopropanol solutions containing a drop or two of concentrated hydrochloric acid to neutralize the remaining absorbed caustic soda. The sponges were then subjected to a washing treatment by squeezing them several times while immersed in azeotropic isopropanol, removing and pressing them to expel excess liquid and repeating the procedure 3 additional times, each time using fresh azeotropic isopropanol to remove the reaction liquor and salt. Following the fourth washing, the sponges were washed with 100% isopropanol and after pressing out excess isopropanol, the sponges were dried in an air circulating oven at about 45° C. As a control, three 1.8 gm. samples of sponge were subjected to washings with azeotropic isopropanol and 100% isopropanol and dried in an air circulating oven at about 45° C. Properties of the sponges are shown in Table III.

It will be noted that in the formation of derivatized sponges of about the same DS values as those of the fibers, lesser amounts of chloroacetic acid were used. The regenerated cellulose has a degree of polymerization of about one-quarter that of the wood pulp fibers and, hence, the smaller the amounts of the acid to form derivatives of about the same DS.

As shown by the data, the reaction of the sponge structures to saline solution follows the reaction of the fibers to such aqueous liquid. It is pertinent to note that when the sponges are wetted with the aqueous liquid, the "hairs" at cut surfaces disappear and the sharp cut edges become swollen and blunted, the higher the DS the greater the degree of swelling. At the upper DS, the sponge becomes so highly swollen it approaches a gel state.

Derivatized cellulose sponges having higher liquid absorbencies may be prepared by mixing with the viscose, preferably prior to the addition of the fibers and pore forming salt, an alkali-soluble polyacrylate or polymethacrylate or copolymer of acrylic and methacrylic acids. The amount of acrylic additive may vary from about 1 to 15%, preferably 7 to 10%, based on the cellulose. An example of a satisfactory additive of this class is the Rohm and Haas Co., commercially available Acrysol ASE-108, a 20% solution having a Brookfield LVF viscosity at 25° C. (#1 spindle, 12 rpm.) of 200 cps. The mixture of the addition of the fibers and pore forming salt is then cast, the cellulose solution coagulated, the cellulose regenerated and treated as above described.

As an alternative, starch, particularly amylose starch, such as, for example, National Starch and Chemical Corporation Hylon VII (70% amylose content), may be used as an additive. Following regeneration of the cellulose to form the cellulose-starch sponge structure, the sponge may be derivatized as described above. An effective hemostatic product may be obtained by first preparing a methyl derivative followed by forming a succinyl derivative of the cellulose and amylose.

As an alternative for the production of products having highly efficaceous hemostatic properties, chitin (a poly-$\beta$-(1→4)-N-acetyl-D-glucosamine), a polyhydroxyl biopolymer similar to cellulose, may be added to the viscose prior to the addition of the reinforcing fibers and pore-forming salt. The amount of chitin added may vary up to about 30%, preferably 7 to 15%, based on the cellulose. The sponge is prepared in the conventional manner. In forming a derivative, for example, the cellulose and chitin both become derivatized, as in preparing a succinyl derivative which is a highly effective hemostat.

In producing derivatized products, either fibrous or sponge structures, the base material may be converted first into a methyl derivative of the desired DS. The methyl derivative is then converted into a hydroxypropylmethyl derivative or into a succinylated methyl derivative or succinylated hydroxypropulmethyl derivative of desired DS. It is obvious that the specific derivatized cellulose structure may be prepared with specific substitutents based upon the intended use for the structure and the desired properties of the structure.

Coherent structures, both fibrous mat and sponge forms may be impregnated with azeotropic isopropanol or ethanol solutions containing gel-free, water-soluble and aqueous isopropanol or aqueous ethanol soluble hydroxypropylmethyl cellulose and methyl cellulose. Such hydroxypropylmethyl cellulose compounds have a hydroxypropyl DS of about 0.11–0.30 and a methyl DS of about 1.5–2.2. The methyl cellulose derivatives have a DS of about 1.5–2.2. The impregnating solutions may contain from about 0.02 to about 0.20% of the desired impregnant. Following impregnation, the cellulose derivative impregnant may be precipitated within the structure by immersion of the impregnated structure in 100% isopropanol, or 100% ethanol. After draining, the impregnated structures are vacuum dried at about 45° C.

If desired, the vacuum dried structures may be compacted without decreasing the absorbency of the structures. The vacuum dried structures are conditioned to contain between about 7 and 15% moisture which may be effected by maintaining the structures in ambient atmosphere at about 23° C. and a RH of about 50% for 24 hours. The fibrous mat structures may be pressed to reduce the thickness to 40 to 60% of the original thickness of the conditioned mats. In the case of sponge structures, they may be reduced by as much as 90% of the original thickness.

In the dried or dried and compacted structures, the impregnants function as dry binders. Upon wetting these structures with aqueous liquids, such as body liquids, the water soluble derivatives dissolve and are released. For example, pledgets when used in eye treatments and dabbed on the eye, absorb rapidly the liquid, swell, the derivative dissolves and is released into the tear. The released derivative serves as a lubricant and cushioning agent. Depending upon the DS of the cellulose base structure, the macrofibrils and microfibrils become highly swollen and may also dissolve, thus there may be a dual source of water-soluble material to function as a soothing lubricant. Other water-soluble dry binders satisfactory include hydroxypropylmethyl cellulose, carrageenin, alginates, dextran and the like may be used in lieu of the above used agents.

If desired the structures also may be impregnated with aqueous isopropanol or ethanol solutions of germicides, moldicides, bacteriocides, pharmaceuticals and the like, such as, for example, bacitrin, proccine, methiolate, ephedrine, cortisone, iodine and carbacol. Obviously, upon drying the structures, these agents remain within the structure. Upon wetting as with an aqueous body liquid, the agent dissolves and is slowly released.

EXAMPLE 7

Coherent structures, both fibrous mat and sponge forms, were impregnated with azeotropic ethanol solutions containing gel-free, aqueous ethanol soluble hydroxypropylmethyl cellulose (hydroxypropyl DS 0.2, methyl DS 1.9) and methyl cellulose (DS 2.3). The fibrous mats were as prepared in accordance with Example 2 and the sponge form, prepared as in Example 7. The impregnating solutions contained about 0.7% of the cellulose derivative. Samples of the fibrous mats were submerged in the impregnating solutions, withdrawn and again immersed in order to insure a complete impregnation of the mats. In the case of the sponge samples, these were immersed in the impregnating solutions and squeezed three times while immersed to insure a complete impregnation. Following the impregnating procedure, the samples were withdrawn and excess liquid allowed to drain. The structures were then immersed in 100% ethanol to precipitate the respective cellulose derivatives in the structures.

After withdrawing the respective structures excess liquid was drained and the structures vacuum dried at about 50° C. to remove the remaining liquid. The vacuum dried samples were allowed to remain in the laboratory ambient atmosphere, 22° C., 50% RH, for about 20 hours. The mat samples had about 10% moisture while the sponge samples had about 12% moisture. The mat samples were compacted from an original thickness of 3 mm. to a finished thickness of 1.5 mm. The sponge samples were compacted from an initial thickness of 0.7 cm. to a finished thickness of about 0.4 cm. The liquid absorbencies of the impregnated and compressed mats and sponges were substantially identical to the liquid absorbencies of the pre-compressed structures.

In general, the fibrous mats of derivatized cellulose fibers exhibit a higher percent water absorption than the sponge forms. This is attributed by the freeness of the fibers to swell when wet with aqueous liquids. In the sponge structures, the structure consists of interconnected film-like units which define pores and, hence, while the fibers in the mat form can swell in all transverse directions, the film-like units can swell in directions only normal to the film surface. Assuming a mat and sponge both of the same weight and approximately the same DS, the mat will exhibit a higher liquid absorbency than the sponge. This is illustrated by the data in Table IV. As will be noted from the Table, the structures absorb at least about 1000%, by weight based upon the dry weight, of water or aqueous liquids.

In determining the percent absorption of liquids, the dry sample is weighed, the sample then immersed in the liquid, the sample after complete wetting is removed and excess liquid drained without pressing. The wet sample is then weighed and the percent absorption calculated from the weight determinations. It will be noted from Table IV that as the DS increases, the percent absorption increases. It will be further noted that as the DS approaches the upper limit of DS 0.35, the percent absorption decreases. This occurs because at the upper DS a portion of the sample is so highly swollen that it is almost in a gel state and such portion drains with the excess absorbed liquid. The values in Table IV are averages of duplicate sample determinations.

It is apparent that the sponge structures including the polyacrylates, chitin derivatives and/or starch derivatives, these additive substances will be intimately and uniformly distributed throughout the sponge along with the cellulose derivative.

TABLE I

| | Example | | | |
|---|---|---|---|---|
| | control | 1 | 2 | 3 |
| Degree of substitution | 0 | 0.11 | 0.24 | 0.33 |
| Pulp, gms. | 30 | 30 | 30 | 30 |
| Azeotropic IPA, gms. | — | 722 | 722 | 722 |
| 20% NaOH soln., gms. | — | 20 | 40 | 60 |
| ClCH$_2$OOH, gms. | — | 2 | 4 | 6 |
| 100% IPA, gms. | — | 8 | 8 | 8 |
| Air dried fiber mats from 0.1% slurries in | | | | |
| Ethanol/water, V/V | 40/66 | 55/45 | 67/33 | 75/25 |
| IPA/water, V/V | 25/75 | 37/63 | 57/43 | 70/30 |
| Freeze dried fiber mats from 10% slurries in | | | | |
| Ethanol/water, V/V | 25/75 | 35/65 | 50/50 | 65/35 |
| IPA/water, V/V | 15/85 | 25/75 | 40/60 | 55/45 |
| All mats coherent, flexible and soft to touch | | | | |
| Size, sq. cm. (Av.) | 36 | 36 | 36 | 36 |
| Thickness, mm. (Av.) | 4.0 | 3.1 | 3.0 | 3.1 |
| Weight, gms. (Av.) | 1.20 | 1.22 | 1.21 | 1.23 |

TABLE IV

Liquid Absorption

| Fibrous Mat Form | | | | |
|---|---|---|---|---|
| Degree of Substitution | Control | 0.11 | 0.24 | 0.33 |
| % Absorption | 1790 | 2410 | 3200 | 1957 |
| Sponge Form | | | | |
| Degree of Substitution | Control | 0.11 | 0.23 | 0.35 |
| % Absorption | 990 | 1090 | 1338 | 939 |

TABLE II

Microscopic observation (400×); Wet with 0.9% saline solution

| | | Example | | |
|---|---|---|---|---|
| | Control | 1 | 2 | 3 |
| Fibers | | | | |
| Lumen width | Retained | Reduced by 20% due to hydration | Reduced by 50% due to swelling | Reduced 80-90% due to swelling |
| Fiber width | Slight | Increased | Increased | Increased |

TABLE II-continued

Microscopic observation (400×); Wet with 0.9% saline solution

| | | Example | | |
|---|---|---|---|---|
| | Control | 1 | 2 | 3 |
| | increase | 5-10% | 15-35% | over 50% some disintegration |
| Pressure-fiber between glass slides | No effect | Small amt of flattening | Flattened | Almost gel-like |
| Mats | | | | |
| Fiber structure | Retained | Retained - slight hydration | Swollen | Highly swollen |
| Fiber ends | Presence of hairs | No hairs visible | No hairs visible | No hairs visible |

TABLE III

| | Examples | | | |
|---|---|---|---|---|
| | Control | 6 | 7 | 8 |
| Degree of substitution | 0 | 0.10 | 0.23 | 0.35 |
| Sponge, wt. gms. | 5.4 | 7.2 | 7.2 | 7.2 |
| Azeotropic IPA, gms. | — | 400 | 400 | 400 |
| 20% NaOH soln., gms. | — | 8 | 13 | 17 |
| ClCH$_2$OOH, gms. | — | 1.2 | 1.6 | 3.0 |
| 100% IPA, gms. | — | 8 | 8 | 8 |
| Microscopic observation (400×), Wet with 0.9% saline solution | | | | |
| Cut edges | Hairs and sharp cut edges | No hairs, blunted cut edges | No hairs, swollen edges | No hairs, edges highly swollen, partially gelatinized |
| Pore structure | Rigid pores | Rigid pores size as in control | Swollen, coherent, pores smaller | Swollen, almost complete breakdown of pores |
| Physical structure, wet state | Coherent, resilient, retains structure | Coherent, resilient, retains structure | Coherent, loses resiliency upon compressing | Breakdown of structure into gel. |
| Dried from wet state | Coherent, resilient, retains structure | Coherent, resilient, retains structure | Coherent, partial loss of structure | Complete loss of structure |

What is claimed is:

1. Absorbent, coherent, flexible cellulosic structures for application to the body comprising water-insoluble cellulose derivatives of the group of cellulose ethers, cellulose mixed ethers and cellulose ether mixed esters prepared from highly fibrillated, chemically purified wood pulp having a CSF not exceeding about 150, the cellulose derivative having a total DS of between about 0.05 to about 0.35, said structures being further characterized in that when applied to the body and wet with aqueous body liquid the protruding fibrils and microfibrils on the surfaces and along the edges of the structures become highly swollen almost instantaneously whereby the structures are non-irritating to the body over the area to which the structure is applied and in having a higher liquid absorbency than a like structure formed from underivatized, unfibrillated cellulose.

2. The structure as defined in claim 1 wherein the cellulose derivative has a total DS of between 0.1 and 0.25.

3. The structure as defined in claim 1 wherein the protruding fibrils and microfibrils upon becoming swollen dissolve in the body liquid.

4. The structure as defined in claim 1 further characterized by including a water-soluble dry binder whereby upon absorption of body liquid by the structure the dry binder dissolves and is leached from the structure.

5. The structure as defined in claim 1 in the form of a fibrous sheet.

6. The structure as defined in claim 1 in the form of a porous sponge containing up to about 25% of derivatized highly fibrillated, chemical purified wood pulp fibers.

7. The structure as defined in claim 1 being further characterized in absorbing at least 1000% water by weight based upon the dry weight of the structure.

8. The structure as defined in claim 1 wherein the cellulose derivative is carboxymethyl cellulose prepared from highly fibrillated, chemically purified wood pulp having a CSF about 50.

9. The structure as defined in claim 1 wherein the cellulose derivative is hydroxypropylmethyl cellulose prepared from highly fibrillated, chemically purified wood pulp having a CSF about 50.

10. The structure as defined in claim 1 wherein the cellulose derivative is succinylated methyl cellulose or succinylated hydroxypropylmethyl cellulose and the structure being further characterized by exhibiting hemostatic properties.

11. The structure as defined in claim 1 in the form of a porous sponge and being further characterized by including an alkali soluble polyacrylate.

12. The structure as defined in claim 1 in the form of a porous sponge and being further characterized by including chitin derivatives of the group chitin ethers, chitin mixed ethers and chitin ether mixed esters and by exhibiting hemostatic properties.

13. The structure as defined in claim 1 in the form of a sponge wherein the cellulose derivative is succinylated methyl cellulose or succinylated hydroxypropylmethyl cellulose and the structure being further characterized by including succinylated starch or succinylated hydroxypropylmethyl starch and by exhibiting hemostatic properties.

14. The structure as defined in claim 1 further characterized by including an aqueous isopropanol or aqueous ethanol soluble germicide, moldicide, bacteriocide or pharmaceutical agent.

* * * * *